(12) United States Patent
Haldeman

(10) Patent No.: US 6,704,590 B2
(45) Date of Patent: Mar. 9, 2004

(54) DOPPLER GUIDING CATHETER USING SENSED BLOOD TURBULENCE LEVELS

(75) Inventor: Paul Craig Haldeman, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/117,434

(22) Filed: Apr. 5, 2002

(65) Prior Publication Data

US 2003/0191392 A1 Oct. 9, 2003

(51) Int. Cl.[7] .............. A61B 5/05; A61B 8/06
(52) U.S. Cl. ............ 600/407; 600/454; 600/479
(58) Field of Search .................. 600/433–435, 600/585, 455, 437, 459, 461, 462, 407, 479, 454; 604/93.01, 264, 523; 356/336; 73/861.29

(56) References Cited

U.S. PATENT DOCUMENTS

| 4,665,925 A | | 5/1987 | Millar | |
|---|---|---|---|---|
| 4,733,669 A | * | 3/1988 | Segal | 600/585 |
| 4,771,788 A | * | 9/1988 | Millar | 600/455 |
| 4,850,358 A | * | 7/1989 | Millar | 600/486 |
| 5,040,548 A | * | 8/1991 | Yock | 128/898 |
| 5,058,595 A | | 10/1991 | Kern | |
| 5,144,955 A | | 9/1992 | O'Hara | |
| 5,190,045 A | | 3/1993 | Frazin | |
| 5,220,924 A | | 6/1993 | Frazin | |
| 5,246,007 A | * | 9/1993 | Frisbie et al. | 600/465 |
| 5,345,940 A | | 9/1994 | Seward et al. | |
| 5,394,876 A | * | 3/1995 | Ma | 600/455 |
| 5,662,115 A | * | 9/1997 | Torp et al. | 600/455 |
| 5,836,882 A | | 11/1998 | Frazin | |
| 6,083,170 A | * | 7/2000 | Ben-Haim | 600/463 |
| 6,132,379 A | | 10/2000 | Patacsil et al. | |
| 6,166,806 A | * | 12/2000 | Tjin | 356/336 |
| 6,167,765 B1 | | 1/2001 | Weitzel | |
| 6,277,077 B1 | | 8/2001 | Brisken et al. | |
| 6,306,097 B1 | | 10/2001 | Park et al. | |
| 6,325,762 B1 | | 12/2001 | Tjin | |
| 6,355,026 B1 | * | 3/2002 | Mick | 604/523 |
| 6,379,303 B1 | * | 4/2002 | Seitz et al. | 600/438 |
| 6,487,916 B1 | * | 12/2002 | Gomm et al. | 73/861.29 |
| 6,514,249 B1 | * | 2/2003 | Maguire et al. | 606/41 |

FOREIGN PATENT DOCUMENTS

| EP | 0787977 A2 A3 | 7/1997 |
|---|---|---|
| WO | WO 93/08863 A | 5/1999 |

* cited by examiner

*Primary Examiner*—Francis J. Jaworski
(74) *Attorney, Agent, or Firm*—Crawford Maunu PLLC (57) ABSTRACT

A guiding catheter includes a Doppler sensor disposed at a distal end of a flexible shaft. The Doppler sensor can sense a blood flow turbulence level within a chamber of the heart or a blood vessel of the heart. Detecting changes in a blood flow turbulence level is used to assist guiding of the distal end of the flexible shaft. The Doppler sensor may include a piezoelectric sensor or an optical sensor. The sensor readings may be processed to show turbulence through a time domain or frequency domain presentation of velocity. The sensor readings can be used to modulate an audible waveform to indicate turbulence. The guiding catheter may further include steering apparatus enabling deflection of the distal tip.

36 Claims, 5 Drawing Sheets

Section 1-1

DOPPLER GUIDING CATHETER USING SENSED BLOOD TURBULENCE LEVELS

FIELD OF THE INVENTION

The invention relates generally to guiding catheters and, more particularly, to Doppler assisted guiding catheters useful for locating and cannulating vessels of a patient's heart.

BACKGROUND OF THE INVENTION

Catheters are used in a wide variety of medical procedures. In some applications, these devices provide physicians the ability to explore, operate, and insert drugs/medical devices in various reaches of the anatomy without invasive surgery. Oftentimes, the catheters have medical devices mounted on the catheter shaft, such as in an electrophysiological (EP) ablation catheter, wherein an ablation electrode is mounted at a distal tip of the catheter. In another application, guiding catheters are used to create an easily navigable pathway to be used for delivery of various payloads such as drugs, therapeutic/diagnostic devices (e.g., EP mapping and ablation electrodes), and implantable devices (e.g., cardiac pacing/defibrillation leads).

Guiding catheter systems are typically configured with a profile that is optimized for the intended method of access. For example, when trying to access the coronary sinus of a patient's heart, one method is to enter the venous system through an incision at a large vein such as the subclavian vein near the shoulder. A guiding catheter is inserted through this incision and is displaced in an arced path through the superior vena cava into the right atrium of the heart. From the right atrium, the ostium of the coronary sinus must be located. A catheter with a distal contour including a relatively sharp bend will point the catheter towards the likely location of the coronary sinus once the right atrium is reached. The contours of pre-shaped guiding catheters are often fixed during manufacture.

A pre-shaped guiding catheter is sometimes used to blindly locate the coronary sinus ostium. This endeavor, however, is complicated by the fact that the location of the coronary sinus ostium may vary appreciably from one patient to another, especially among patients with diseased hearts. Further, the size and flexibility of the catheter that provides maneuverability through the convoluted access path becomes a disadvantage when trying to manipulate the distal end of the catheter in the right atrium.

The primary goal of a guiding catheter procedure is to locate and cannulate a vessel of interest safely and in the least amount of time. Finding and cannulating the coronary sinus, for example, can become a time consuming, trial and error procedure even in a healthy patient. Patients exhibiting symptoms of advanced heart disease can have blockages or deformations of heart structure, further complicating the task of locating the ostium.

Some common techniques are used to aid the physician in visualizing the distal end of a guiding catheter during cannulation. These techniques include the procedures of angiography and venography. The procedures involve injecting a radioopaque dye into the bloodstream to X-ray map blood vessels. Typically, the catheter is radioopaque as well in order to be clearly located. Although effective, this method requires exposing the patient to radiation, and therefore exposure times are necessarily limited. Further, injection of the dye can cause local thrombophlebitis, though this is now rare with modern contrast agents.

Another approach used in assisting catheter guidance is endoscopy, a technique using a fiber optic camera to visualize the blood vessel interior. This method can be effective, but is expensive and is not always adaptable to the geometries required of a guiding catheter intended for applications such as right heart access.

There is a need for an improved guiding catheter allowing quicker access to vessels such as the coronary sinus. There is a need for a simplified method of identifying such vessels and assisting a physician in cannulating a target vessel with a guiding catheter. The present invention fulfills these and other needs, and addresses other deficiencies of prior art implementations and techniques.

SUMMARY OF THE INVENTION

The invention relates to a guiding catheter which employs Doppler sensing for accessing various anatomical regions, particularly certain regions of the heart. In one embodiment, a guiding catheter used for locating a patient's circulatory structure includes a flexible shaft. A Doppler sensor is disposed at a distal end of the flexible shaft. The Doppler sensor senses a blood flow turbulence within a patient's blood vessel accessed by the distal end of the flexible shaft. The sensed blood flow turbulence indicates a direction to move the distal end of the flexible shaft to locate the patient's circulatory structure. A communication medium is coupled with the Doppler sensor. The communication medium effects transmission of a Doppler sensor reading to a proximal end of the flexible shaft.

According to one configuration, a processing device is coupled to the communication medium. The processing device processes the sensed blood flow velocity to indicate a turbulence level. The sensed blood flow turbulence indicates a transition between a turbulent flow and a laminar flow. This transition indicates the presence of the patient's circulatory structure. The Doppler sensor can be arranged to sense one or both of an axial and radial turbulence component. A comparison of the radial and axial turbulence components indicates the presence of the patient's circulatory structure of interest.

In accordance with another embodiment, a method for cannulating a destination blood vessel involves introducing the distal end of a guiding catheter comprising a flexible shaft and a Doppler sensor disposed at a distal end of the flexible shaft into a patient's access vessel. The guiding catheter is distally advanced through a circulatory pathway. Blood flow turbulence readings are monitored from the Doppler sensor of the guiding catheter to indicate the presence of the destination blood vessel. The distal tip of the guiding catheter is guided based on the blood flow turbulence readings to locate the destination blood vessel.

A payload can be delivered through an open lumen of the guiding catheter after cannulating the destination vessel. The payload can be a cardiac pacing lead or an injection of fluid, for example. The destination blood vessel can include the coronary sinus of the patient's heart, and the circulatory pathway can include the right atrium of the patient's heart accessed via the superior vena cava.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A catheter according to the present invention employs one or more distally mounted Doppler sensors to detect flow velocities to assist in locating venous orifices, pathways, and other cardiac structures. According to one embodiment, a catheter of the present invention employs a forward viewing Doppler sensor that detects blood flow velocities in a generally axial direction. In another embodiment, a catheter of the present invention employs a side viewing Doppler sensor for detecting blood flow velocities in a generally lateral or radial direction. According to another embodiment, a catheter of the present invention employs a forward viewing Doppler sensor and a side viewing Doppler sensor for detecting blow flow velocities in generally axial and lateral/radial directions, respectively.

In general terms, a catheter of the present invention employs Doppler sensing to measure characteristics of blood flow velocity in order to locate destination vessels of interest. According to a more particular technique, Doppler sensing is employed at the distal end of a guiding catheter to detect localized turbulence that occurs at the intersection of vessel tributaries so as to aid the physician in directing the guiding catheter to a destination vessel. By providing an indication of vessel location, the guiding catheter of the present invention provides advantages over prior art guiding catheters and allows the catheter to be more quickly and accurately guided by a clinician during medical procedures.

By way of example, a catheter of the present invention employing Doppler sensing can be inserted into a chamber of a patient's heart, such as the right atrium. Because blood is dumped into the right atrium from various vessels, the characteristics of blood flow velocity detected within the right atrium indicate generally turbulent blood movement within the right atrium. Blood flow within vessels, such as the coronary sinus, tends to be significantly less turbulent (i.e., more laminar) than that associated with chambers of the heart. As the catheter tip is moved proximate the entrance of a blood vessel of interest, such as the coronary sinus, a change in blood flow velocity characteristics proximate the ostium of the coronary sinus is detected. This change is indicative of a confluence of right atrium and coronary sinus blood flows which tend to become less turbulent as the catheter tip is moved closer to the coronary sinus ostium.

Figure 1:
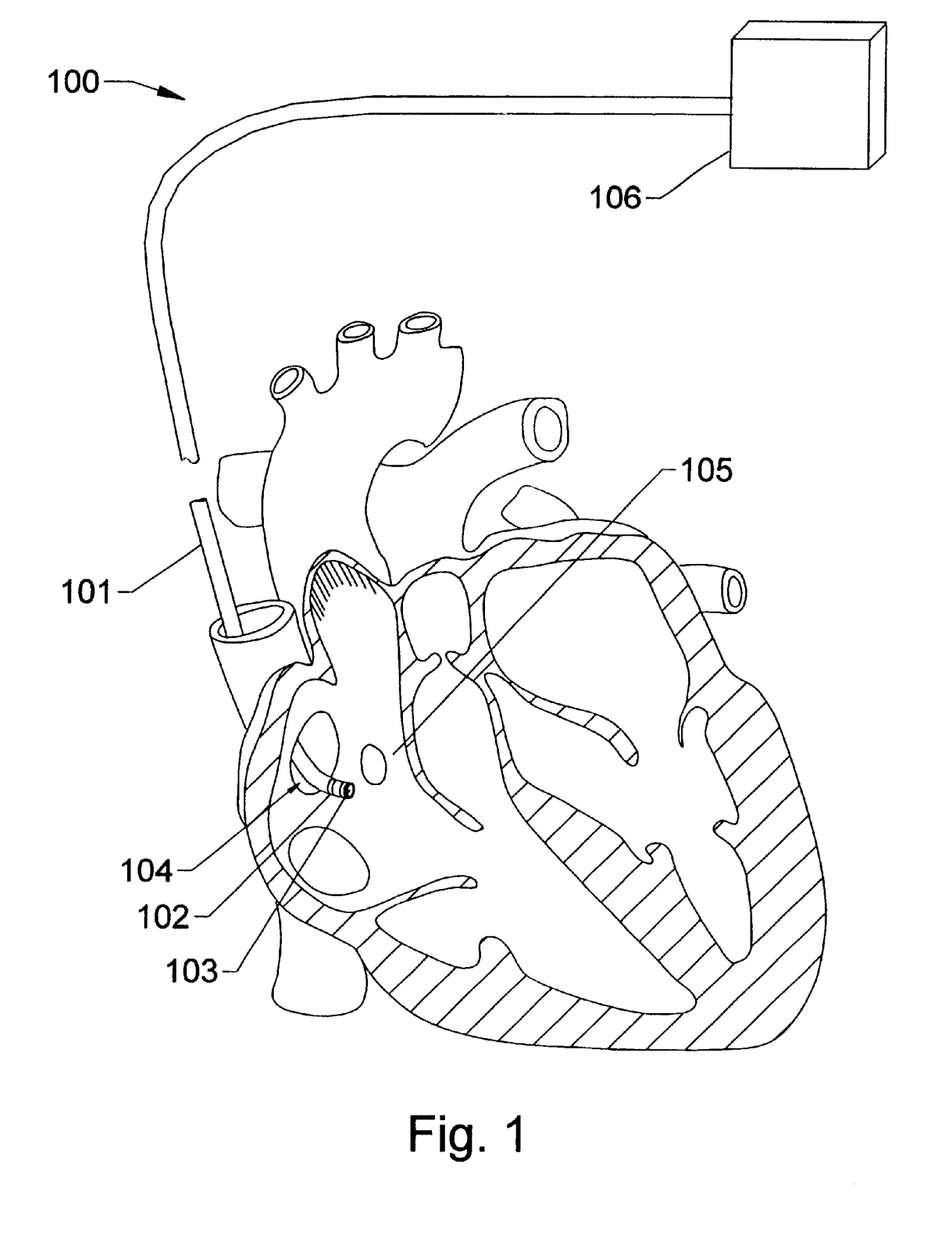
FIG. 1 is a cutaway view of a heart being accessed by a catheter according to the present invention, a distal tip of the catheter located in the right atrium of the heart.

FIG. 1 illustrates a catheter embodying features of the present invention. The catheter, generally indicated by reference numeral 100, includes a flexible shaft 101 and a tip mounted Doppler sensor 102. The flexible shaft 101 has an open guide lumen 103 through which a payload can be introduced. The flexible shaft 101 may also include a pre-shaped distal end 104 optimized for accessing the intended destination. In FIG. 1, the shaft's distal end is located in the right atrium and directed towards the coronary sinus ostium, which is a common destination for pacing/defibrillation leads.

A processing device 106 is attached to a proximal end of the flexible shaft 101. The processing device 106 is coupled to the Doppler sensor 102 and processes the signals generated by the Doppler sensor 102. The processing device 106 typically manipulates and converts Doppler signals such that the signals may be easily interpreted by the clinician, such as by being displayed on a display device. The clinician reads/interprets the Doppler signals and uses the interpreted signals to direct the distal end of the flexible shaft 101.

Figure 2:
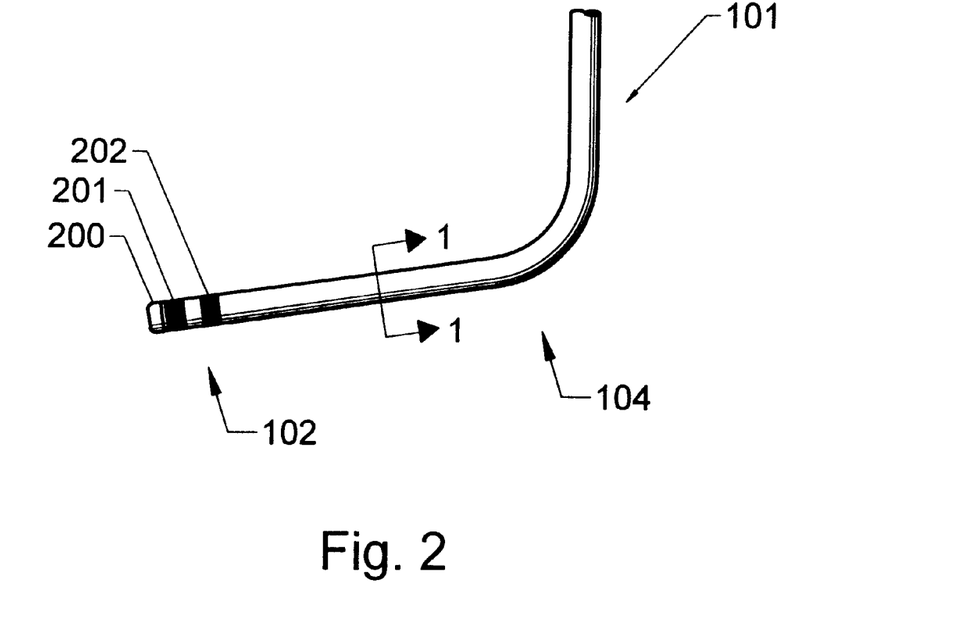
FIG. 2 is an external view of the catheter's distal end showing a tip mounted ultrasonic Doppler sensor according to the present invention.

Referring now to FIG. 2, a view of the distal end of the flexible shaft 101 is shown in greater detail. The flexible shaft 101 in this configuration includes a Doppler sensor 102 having two ultrasonic transducers 201, 202. A soft tip 200 is located at the distal tip to help reduce tissue abrasion during catheter introduction proceedings. The flexible shaft 101 is typically constructed from a tubular material. In applications suited for coronary sinus access via the vasculature into the right atrium, the flexible shaft 101 may be about 40 cm to about 60 cm in length, with diameters ranging from 6 French to 10 French. Guide lumen diameters can range from 0.060" to 0.120" depending on the medical procedure to be performed and the payload to be introduced.

The flexible shaft 101 is typically formed of a medical application polymer. Pebax thermoplastic elastomer resin is a preferred material of choice for catheter shafts. Other polymer materials, such as nylon and polyurethane, are also commonly used for catheter shafts. The flexible shaft 101 may include regions of different material stiffness (e.g., durometer rating) to provide customized performance. In a typical application, a distal region of the flexible shaft 101 is fabricated to be relatively flexible, thereby allowing maneuverability through convoluted paths. A proximal region is made stiffer than the distal region, providing kink resistance and better transmission of axial forces and torque.

The pre-shaped distal end 104 can be thermoset on the flexible shaft 101 in production. If the shaft material does not take a thermoset, a jacket of thermoset or likewise pre-formed material can be enclosed around a distal end of the flexible shaft 101. The jacket causes the distal end 104 to conform to a desired shape. Alternatively, a stylet 302 (best seen in FIG. 3) made of Nitonol or other superelastic material can be affixed (e.g., bonded or enclosed) within a distal portion of the flexible shaft. The superelastic properties of the stylet 302 allow it to be substantially deformed, thereby allowing the distal end 104 to be straightened for guiding through veins and/or arteries, then returning to the preformed shape when a desired access point, such as the right atrium, is reached.

Figure 3:
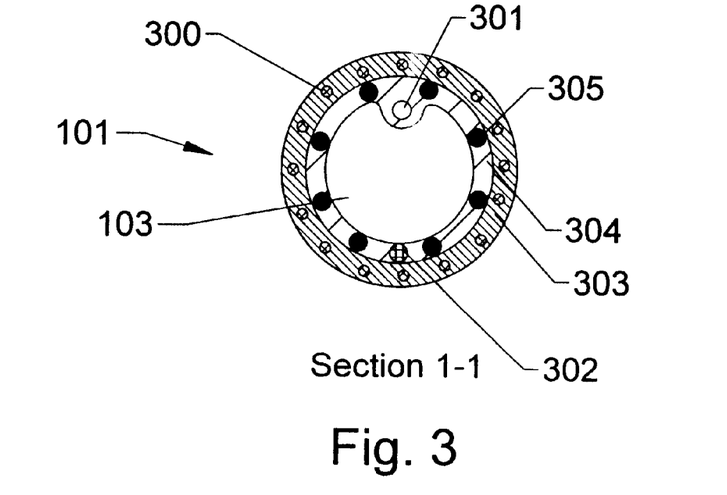
FIG. 3 is a cross sectional view of the catheter corresponding to section 11 in FIG. 2.

A flexible shaft 101 may include a braid 300 as seen in FIG. 3. The braid 300 is typically formed of fine stainless steel wires, although a stainless steel ribbon and/or artificial fibers can also be used to form a braid 300. Such a braid 300 may cover all or part of the flexible shaft 101, improving axial stiffness and kink resistance of the flexible shaft 101 with only a minimal reduction in maneuvering flexibility. The braid 300 can be bonded or otherwise affixed to an exterior surface of the flexible shaft 101. Alternatively, the braid 300 can be molded within the walls of the shaft 101.

As shown in FIG. 3, the braid 300 is embedded in an exterior jacket 303, the jacket 303 surrounding an interior tube 304. The exterior jacket 303 is typically formed of a high durometer rated Pebax that provides a smooth and durable exterior on the flexible shaft 101. The interior tube 304 can be constructed of a material similar to that used in the exterior jacket 303, but is more typically formed from a lubricious material such as PTFE. Forming the interior tube 304 with a lubricious material allows easier passage of payloads (e.g., pacing leads) through the guide lumen 103. Other payloads that can also be introduced into the guide lumen 103 include fluids, such as drugs and contrast media. It is noted that fluid payloads may not require a lubricous lining in the guide lumen 103.

The flexible shaft 101 typically includes at least one guide lumen 103, and may include additional lumens as well. Additional lumens can be used for guide wires, injections, electrical wires, and steering apparatuses, for example. The arrangement shown in FIG. 3 shows an exemplary extra lumen 301. The lumen 301 is extruded into the inner wall of the interior tube 304, although other lumen fabrication methods are possible. In one alternative, the lumen 301 can be formed of a separate tubing and bonded to an inner wall during shaft lay-up.

The flexible shaft 101 includes a communication medium allowing distal Doppler sensor readings to be received at a proximal end of the catheter 100. This communication medium may include conductors 305 in a catheter configuration where the Doppler sensor readings include electrical signals. Conductors 305 can be embedded within the flexible shaft 101 as illustrated in FIG. 3. Other means of deploying conductors 305 may include bonding the conductors 305 to an interior or exterior surface of the flexible shaft. In guiding applications, it is preferred the conductors 305 be restrained to prevent interference with payloads deployed within the lumen 103. It is appreciated, however, that the conductors 305 can also be freely deployed within the lumen 103 in situations where the conductors 305 will not impede passage of a payload through the flexible shaft 101, or when the catheter 100 does not pass a payload through the lumen 103.

Referring back to FIG. 2, the Doppler sensor 102 in this configuration includes tube shaped piezoelectric transducers 201, 202 located near the distal end of the flexible shaft 1. In one arrangement, one transducer 201 can be used as an ultrasonic emitter and the other transducer 202 can be used as a receiver. This configuration is useful for a continuous Doppler configuration. It is appreciated that both emitter and receiver can be integrated into a single piezoelectric device. Such integral transducers are typically used for pulsed Doppler applications. The emitter generates a localized ultrasonic signal which is reflected off the blood flowing around the catheter tip. This reflected signal is then sensed by the receiver and is communicated back to equipment at the proximal end of the catheter 100. Frequencies of the ultrasonic transducers can range from 1 to 10 MHz, although 5 to 8 MHz is a more commonly used range for medical applications.

The transducers 201, 202 are preferably flush mounted (e.g., bonded or embedded) to the flexible shaft 101. This keeps the shaft's outer surface smooth and allows the flexible shaft 101 to more easily traverse blood vessels. The transducers 201, 202 are coupled (e.g., soldered) to the conductors 305 during shaft lay-up. The transducers 201, 202 are typically composed of a PZT piezoceramic or piezocomposite material bonded to a metal case or cylinder. If tubular transducers are employed, the transducers can be configured to vibrate axially (e.g., a contraction of tube's length) and or radially (e.g., a contraction of the diameter of the tube). This characteristic of tubular transducers can be advantageously used to detect axial and radial components of velocity.

Figure 4:
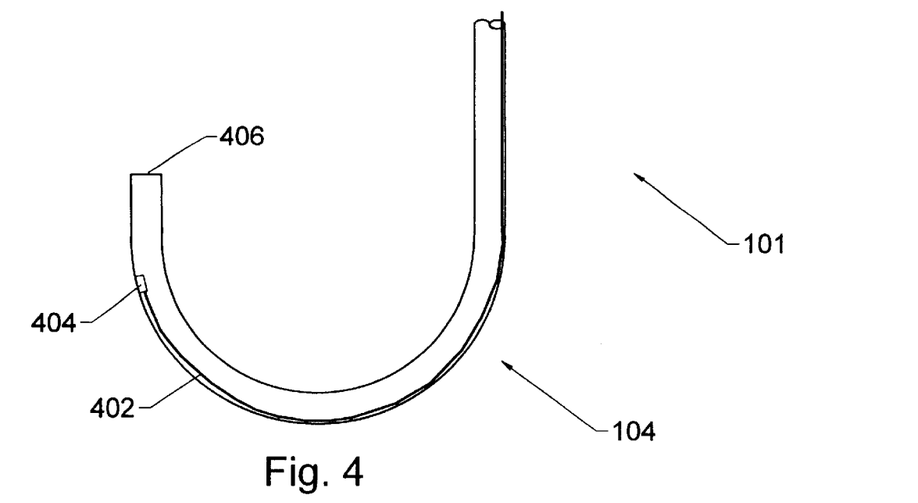
FIG. 4 is a view of a distal end of the catheter showing a steering mechanism according to one configuration of the present invention.
Figure 5:
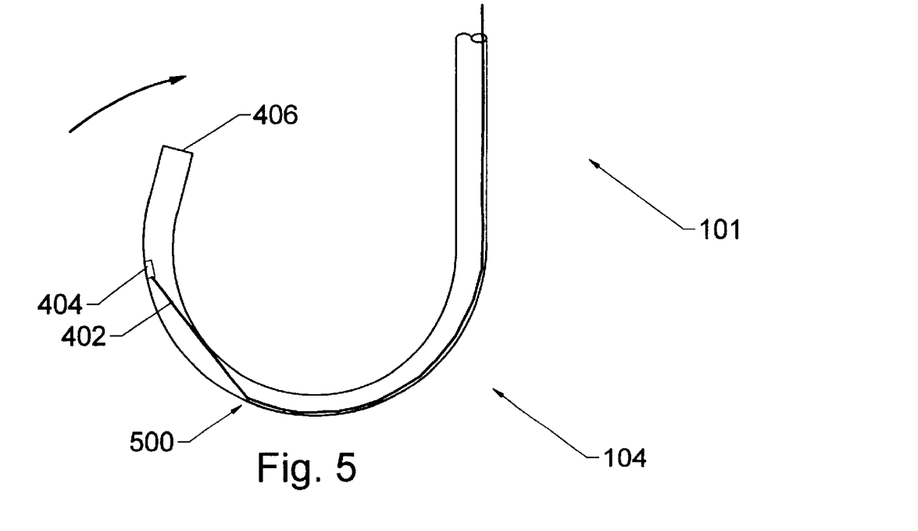
FIG. 5 is a view of a distal end of the catheter of FIG. 4, showing a deflected orientation of the distal tip.

A useful adaptation to the catheter 100 includes a steering apparatus deployed within the flexible shaft 101. A steering apparatus allows the clinician to deflect a distal end of the catheter 100 during cannulation, and can effectively enhance the ability to access vessels. As illustrated in FIG. 4, the steering apparatus can include a structural mechanism such as a steering tendon 402 connected to a section of the flexible tube 101 at an attachment point 404 distal to the pre-formed end 104. The steering tendon 402 is radially restrained through at least part of the flexible shaft 101, typically slidably deployed within a lumen. As shown in FIG. 5, the tendon 402 is unrestrained between the attachment point 404 and an anchor point 500. A tensile force applied to a proximal end of the steering tendon 402 causes a deflection of the distal tip 406 is indicated by the arrow in FIG. 5. The desired deflection shape can be modified by varying the attachment point 404 and an anchor point 500. The steering tendon 402 is allowed to move freely within the flexible shaft between the attachment point 404 and anchor point 500.

Figure 6:
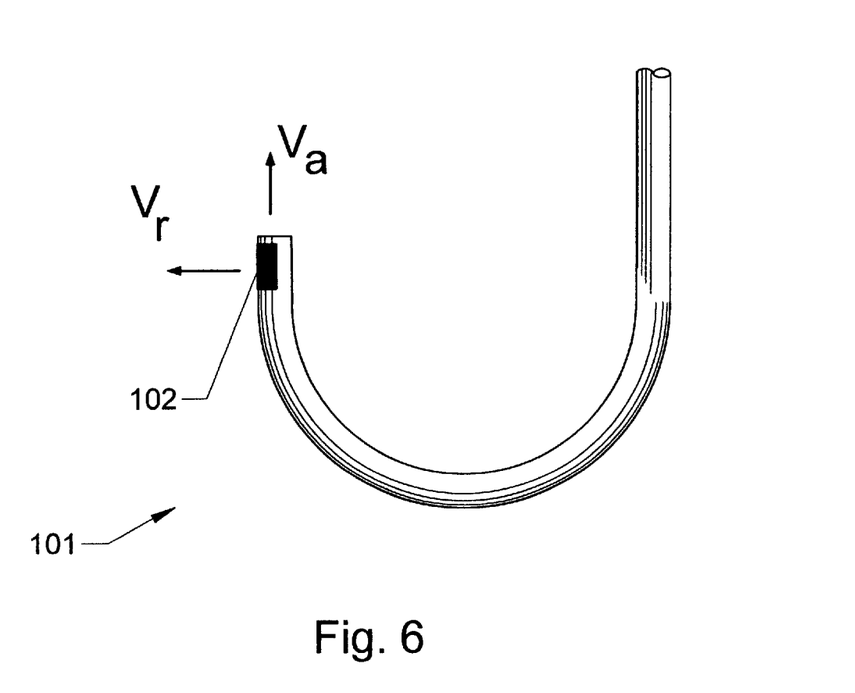
FIG. 6 is a view of a catheter's distal end showing a pre-shaped curve and a side-viewing Doppler sensor according to an embodiment of the present invention.

Another useful configuration of a flexible shaft 101 is shown in FIG. 6. In this configuration, the pre-formed distal end 104 is a substantially J-shaped curve. The Doppler sensor 102 can be a planar or curved ultrasonic sensor disposed on a partial outer surface of the flexible shaft 101. In such a setup, the Doppler sensor 102 is mounted with a field of view such that it primarily detects radial velocity components ($V_r$) according to the principles of Doppler velocimetry. FIG. 6 illustrates the relative radial ($V_r$) and axial ($V_a$) velocity components that can be discerned by using axial and radial sense signals produced by a Doppler sensor 102.

A configuration measuring at least radial velocity components, $V_r$ is particularly suited for finding a branch vessel from an access vessel. When the flexible shaft 101 is deployed within the access vessel, the mean velocity component of access vessel flow will be $V_a$. Mean blood flow in from a branch vessel will have higher $V_r$ velocity components relative to the deployed catheter 100, since the branch vessel connects off-axis with the access vessel. It is advantageous to measure velocity and turbulence from $V_r$ to locate the branch vessel. Alternatively, a system can use a Doppler sensor to measure both $V_r$ and $V_a$ components, and compare the relative velocity and turbulence levels of these components to locate a branch vessel.

The fundamentals of Doppler theory in relation to measuring fluid velocities are well known. The Doppler effect causes the observed frequency of a source to differ from the radiated frequency of the source if there is motion that results in increasing or decreasing the distance between the source and the observer. In practice, the Doppler effect is exploited by measuring frequency shifts of waves that are transmitted from the observer and reflected back to the observer from a moving object (e.g., a particle moving within a fluid). The measured frequency shifts are proportional to velocity components normal to the plane of the emitted waves.

Figure 7:
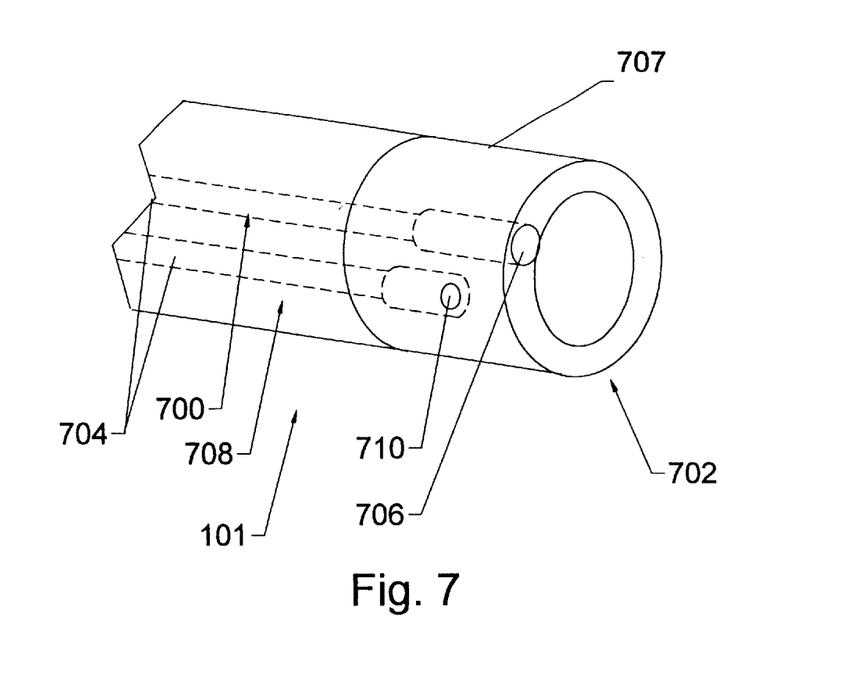
FIG. 7 is a perspective view of a catheter's distal end showing a tip mounted fiber optic Doppler sensor according to an embodiment of the present invention.

Although ultrasonic transducers are relatively inexpensive and well known in the medical arts, optical Doppler sensors are also widely used to measure fluid velocities. Referring now to FIG. 7, an embodiment of a flexible shaft 101 utilizing an optical Doppler sensor 102 is illustrated. The Doppler sensor 102 includes a fiber optic sensor 700 that emits and reflects light waves off of the blood localized at the distal tip 702 of the flexible shaft 101. In this configuration, a fiber 704 acts as a communication medium for sensor inputs/outputs and is disposed within the flexible shaft 101 where it can be accessed at a proximal end. The fiber optic sensor 700 includes a lens assembly 706 at a distal end 707. The fiber 704 carries the light source from the proximal end to the lens assembly 706. In this embodiment, the lens assembly 706 acts as a both an emitter and a receiver.

To obtain radial velocity measurements from an optical device, a side-facing fiber optic sensor 708 can be utilized. The fiber optic sensor 708 includes a side-facing lens assembly 710 coupled to an optical fiber 704. The side facing lens assembly 710 includes an optical reflector to orient the transmitted and received light waves in the appropriate directions. Alternate embodiments of this invention can include a plurality of fiber optic sensors 700, 708 embedded within the flexible shaft 101 and distal end 707, wherein the two or more fiber optic sensors perform the receiving and emitting tasks separately.

The processing device 106 for a fiber optic Doppler sensor 700, 708 can include a laser light source and receiving optics. The processing device 106 detects the frequency shift of the reflected light and characterizes the velocity for easy display and interpretation by the physician.

The apparatus and methods used for processing Doppler signals are well known in the art for both ultrasound and optical apparatus. Various methods of emitting radiated waves and receiving reflected waves are known, in particular continuous wave Doppler and pulsed Doppler. Continuous wave Doppler involves emitting a continuous ultrasonic wave at an emitter and receiving a scattered signal at the receiver. A Doppler frequency shift is detected and the frequency shift magnitude is registered at the processing device 106. The processing device 106 allows the physician to observe real time changes of blood flow velocity at or near the catheter's distal tip in order to help guide the catheter 100 towards its destination.

Another form of Doppler processing includes pulsed Doppler. Pulsed Doppler involves alternating between transmitting and receiving waves of energy. Unlike continuous wave Doppler, which provides a spectral array that represents the entire cross section of the blood vessel, the pulsed Doppler provides a spectral pattern obtained from a small sample volume within the blood vessel. Simultaneous Doppler information and real time imaging may be obtained without interruption of either modality (continuous and pulsed). Because the pulsed Doppler method provides the Doppler shifted frequency data from a small sample volume within the blood vessel (as opposed to the entire diameter of the vessel obtained with the continuous wave Doppler), the range of frequencies displayed in the normal artery is less with the pulsed technique. Pulsed Doppler is therefore, more sensitive to determining the presence of turbulent flow, such as that which occurs near to a stenosis (spectral broadening).

The Doppler sensor data is primarily used to measure instantaneous local fluid velocities. A system according to the present invention uses the measured velocities to determine blood flow turbulence. In particular, the invention is directed towards detecting a transition from a relatively turbulent blood flow to a relatively laminar blood flow (and vice-versa), as well as detecting varying degrees of blood turbulence. Since blood turbulence characteristics change at blood vessels intersections, a device according to the present invention can detect branches by sensing and processing levels of local turbulence (e.g., turbulence at or near the catheter's distal tip). These turbulence readings can advantageously be utilized to assist in directing a distal end of the catheter 100 to the desired destination vessel.

The principles of turbulent fluid flow are well known in the art. In general, flow is classified as laminar and turbulent on the basis of internal flow structure. Laminar flow is characterized by smooth motion in the direction of mean flow in laminae or layers. Turbulent flow is characterized by random, three-dimensional motions of fluid particles superimposed on the mean flow motion.

The nature of incompressible flow (laminar or turbulent) can be characterized by a dimensionless variable known as the Reynolds number (Re). The Reynolds number is calculated from mean velocity and kinematic viscosity of the fluid as well as a size parameter (e.g., diameter) of the vessel carrying the fluid. Transition from laminar to turbulent flow has been observed in ranges from 2000<Re<5000, and may be dependent on other factors not calculated in the Re, such as vessel smoothness and external vibration/stimuli. Discussions of turbulence as relating to the present invention are not intended to describe turbulence only as characterized by the Reynolds number, but are directed towards measurable random variations in mean flow velocities. This may include variations in velocities caused by mixing of fluid at intersecting blood vessels, even if flow within both vessels can be characterized as laminar by the Reynolds number.

Figure 8:
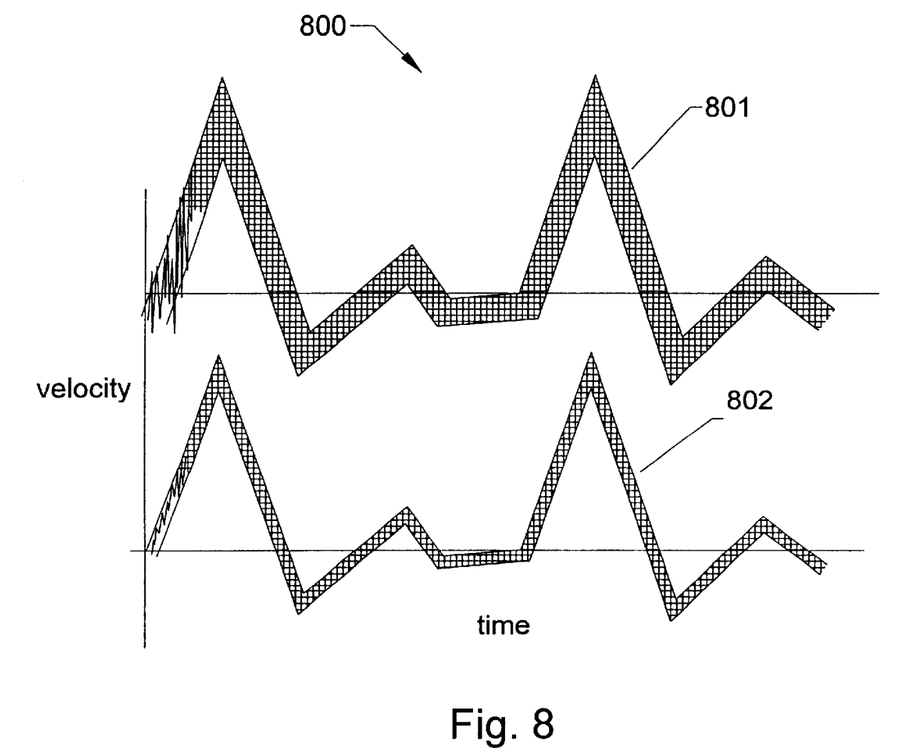
FIG. 8 is a plot of velocity versus time comparing representational views of turbulent and laminar flow from a Doppler sensor according to the present invention.

An exemplary velocity measurement as might be seen during catheter cannulation proceedings is shown in FIG. 8. The graph 800 represents a time varying velocity plot as might be seen from processed Doppler sensor readings. The top plot 801 indicates a turbulent flow. The general shape of the plot 801 conforms to systolic and diastolic mean velocity flows in the cardiac cycle that may be seen in any active heart vessel. The plot 801 has relatively large random variations in instantaneous velocity, and this is indicated by the shaded line. The shaded line is relatively thick and envelops some portion (e.g., $95^{th}$ percentile) of instantaneous velocity maxima and minima at any given time. The bottom plot 802 has a smaller shaded area indicating a smaller envelope of instantaneous velocity variation. The plot 802 can thereby be interpreted to be less turbulent than plot 801. As a practical matter, there will usually be some small amount of random fluctuation in the plot 802 due to system noise, even in purely laminar flow. However, the relative thicknesses of plots 801 and 802 can allow an experienced clinician to make determinations of relative turbulence.

Figure 9:
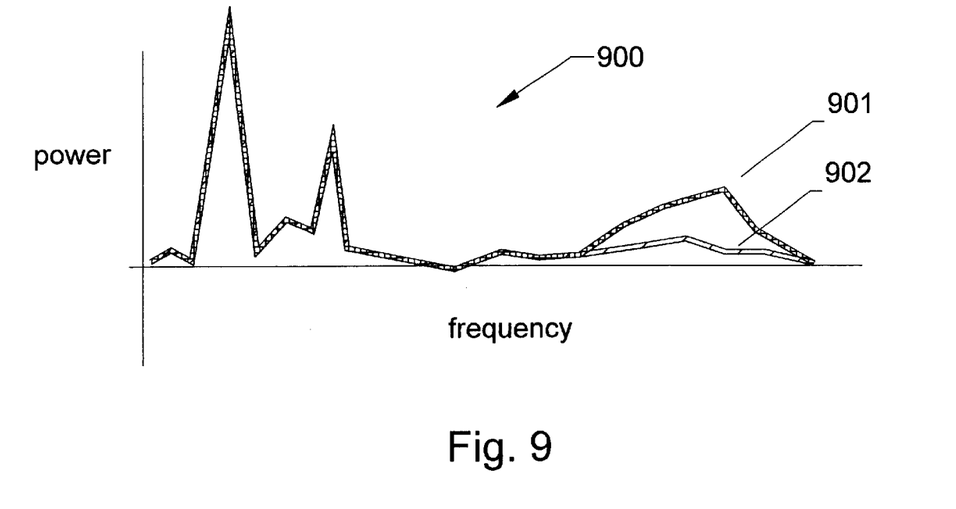
FIG. 9 is a power versus frequency plot as obtained from Doppler velocity information comparing frequency representations of turbulent and laminar flows.

FIG. 9 represents the time varying data as seen in FIG. 8 translated to a frequency domain graph 900. The plots 901 and 902 both have large low frequency components relating to the mean flow caused by velocities in the normal cardiac cycle. The plot 901 has a peak at high frequency, whereas this peak is much lower for plot 902. This is another indication that the Doppler velocity reading represented by plot 901 is more turbulent than that shown for plot 902. Frequency spectra as seen in FIG. 9 can be processed and displayed in real time using devices well known in the art.

The transformation of time domain data to frequency domain data is typically accomplished by processors using algorithms such as a Fast Fourier Transform (FFT). In a system according the to present invention, a graphical display of time varying graph 800 and/or frequency domain graph 900 can be displayed (e.g., computer display) to the clinician during cannulation proceedings. The display is updated real-time as the catheter 100 is advanced, and the clinician can utilize changes in turbulence readings as described to indicate the presence of a branching vessel.

In is recognized that other means of indicating turbulence from the Doppler velocity readings can also be used according to the present invention. In another embodiment, the instantaneous velocity signal is processed and used to modulate an audible sinusoidal tone. The velocity signal can be passed through a high pass filter such that only higher frequency components of velocity would modulate the tone. In this way, the mean velocity associated with the cardiac cycle would not significantly affect the signal modulation. In some cases, it may be advantageous to extract the mean flow velocity components before filtering, as the presence of this component is indicative that the sensor is in an active blood vessel and not at a blockage or void where little or no flow is being measured.

When a more turbulent flow is encountered (e.g., within the right atrium), the audible tone would be modulated with components of turbulence and thereby contain high frequency noise. This causes the audible tone to take on some aspects of white noise. In contrast, when the sensor is in laminar flow regimes (e.g., proximate the coronary sinus ostium or within the coronary sinus), the tone would sound more like a pure sine wave. As the human ear is very sensitive to changes in audible signal quality, using an audible tone to determine turbulence levels can be very effective. Further, the use of audio information allows the clinician to concentrate his or her eyes on the patient, apparatus and/or other instruments, and thereby more effectively complete the cannulation procedure.

In one example of a cannulation procedure, the clinician advances a catheter 100 according to the present invention into the right atrium of the heart, such as illustrated in FIG. 1. Since various vessels, including the coronary sinus 105, empty into the right atrium, a measurable amount of turbulent activity will be present in the majority of the right atrium. As the Doppler sensor 102 approaches the coronary sinus 105, the flow becomes less turbulent, as the flow exiting near the coronary sinus 105 will resemble the more orderly, and possible laminar, flow within the coronary sinus 105. The indication of less turbulent or laminar flow can provide cues to the clinician in that a desired branch vessel is nearby to the distal tip of the guiding catheter 100.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guiding catheter used for locating a patient's circulatory structure, comprising:
    a flexible shaft having an open lumen dimensioned for receiving a payload; and
    a detector comprising a Doppler sensor disposed at a distal end of the flexible shaft, the Doppler sensor sensing blood flow velocity within the patient's circulatory structure accessed by the distal end of the flexible shaft, the detector producing blood flow turbulence information indicative of a transition between laminar blood flow and turbulent blood flow, wherein the transition between laminar and turbulent blood flow is indicative of a relative change in position of the flexible shaft's distal end between cardiac vessel and cardiac chamber locations.

2. The guiding catheter according to claim 1, wherein the Doppler sensor is arranged to sense a radial and an axial turbulence component, the detector performing a comparison of the radial and axial turbulence components to produce the blood flow turbulence information.

3. The guiding catheter according to claim 1, wherein the sensed blood flow velocity is transformed to a frequency response indicative of blood flow turbulence.

4. The guiding catheter according to claim 1, wherein the Doppler sensor is mounted at the distal end of the flexible shaft to have a radially directed field of view.

5. The guiding catheter according to claim 1, wherein the Doppler sensor comprises an emitter and a receiver.

6. The guiding catheter according to claim 5, wherein the emitter of the Doppler sensor comprises an ultrasonic piezoelectric crystal, and the receiver of the Doppler sensor comprises an ultrasonic piezoelectric crystal.

7. The guiding catheter according to claim 5, wherein the emitter of the Doppler sensor comprises a laser light source, and the receiver of the Doppler sensor comprises an optical lens.

8. The guiding catheter according to claim 1, further comprising a steering mechanism connected to a distal section of the flexible shaft enabling selectable deflection of the distal end of the flexible shaft.

9. The guiding catheter according to claim 8, wherein the steering mechanism comprises a steering tendon connected to the distal section of the flexible shaft, the steering tendon longitudinally disposed along the flexible shaft and accessible from a proximal end of the shaft.

10. The guiding catheter according to claim 1, wherein the flexible shaft has an outer diameter ranging from about 8 French to about 10 French.

11. The guiding catheter according to claim 1, wherein the open lumen is adapted to receive an implantable cardiac lead.

12. The guiding catheter according to claim 1, wherein the open lumen is adapted to receive an injection of fluid.

13. A method for cannulating a destination blood vessel, comprising:
    introducing the distal end of a guiding catheter comprising a flexible shaft and a Doppler sensor disposed at a distal end of the flexible shaft into a patients access vessel;
    distally advancing the guiding catheter through a circulatory pathway which includes at least a portion of a heart chamber;

monitoring blood flow turbulence readings from the Doppler sensor of the guiding catheter and detecting a transition between turbulent and laminar blood flow using the blood flow turbulence readings; and guiding the distal tip of the guiding catheter based at least in part on the detected transition between turbulent and laminar blood flow to locate the destination blood vessel.

14. The method according to claim 13, wherein monitoring blood flow turbulence readings further comprises deriving a radial and an axial turbulence component from the blood flow turbulence readings, the radial and axial turbulence components used to detect the transition between turbulent and laminar blood flow.

15. The method according to claim 13, wherein monitoring blood flow turbulence comprises measuring a frequency response of blood flow velocity.

16. The method according to claim 13, wherein monitoring blood flow turbulence readings from the Doppler sensor further comprises using pulse Doppler.

17. The method according to claim 13, wherein monitoring blood flow turbulence readings from the Doppler sensor further comprises using continuous wave Doppler.

18. The method according to claim 13, wherein monitoring blood flow turbulence further comprises using an audio signal to detect blood flow turbulence levels.

19. The method according to claim 13, further comprising cannulating the destination blood vessel with the distal end of the guiding catheter after locating the destination blood vessel.

20. The method according to claim 19, further comprising inserting a payload through the guiding catheter into the destination blood vessel after cannulating the destination blood vessel.

21. The method according to claim 20, wherein the payload comprises a cardiac pacing lead.

22. The method according to claim 20, wherein the payload comprises an injection of fluid.

23. The method according to claim 13, wherein the destination blood vessel includes the coronary sinus of the patient's heart.

24. The method according to claim 23, wherein the circulatory pathway includes the right atrium of the patient's heart accessed via the superior vena cava.

25. A system for locating and cannulating a patient's circulatory structure, comprising:
a catheter comprising:
a flexible shaft having an open lumen dimensioned to receive a payload;
a Doppler sensor disposed at a distal end of the flexible shaft, the Doppler sensor sensing blood flow velocity within a patient's circulatory structure accessed by the distal end of the flexible shaft;
a communication medium coupled with the Doppler sensor, the communication medium transmitting the sensed blood flow velocity to a proximal end of the flexible shaft; and
a processing device coupled to the communication medium, the processing device processing the sensed blood flow velocity to produce turbulence level information indicative of a transition between turbulent blood flow and laminar blood flow.

26. The system according to claim 25, wherein the Doppler sensor is arranged to sense a radial and an axial blood flow velocity component, and wherein the processing device processes the radial and axial velocity components to produce the turbulence level information.

27. The system according to claim 25, wherein the processing device transforms the sensed blood flow velocity to a frequency response.

28. The system according to claim 25, wherein the Doppler sensor is mounted at the distal end of the flexible shaft to provide a radially directed field of view.

29. The system according to claim 25, wherein the Doppler sensor comprises an emitter and a receiver.

30. The system according to claim 29, wherein the emitter of the Doppler sensor comprises an ultrasonic piezoelectric crystal, the receiver of the Doppler sensor comprises an ultrasonic piezoelectric crystal, and the communication medium comprises at least one electrical conductor.

31. The system according to claim 29, wherein the emitter of the Doppler sensor comprises a laser light source, the receiver of the Doppler sensor comprises an optical lens, and the communication medium comprises at least one optical fiber.

32. The system according to claim 25, further comprising a steering mechanism connected to a distal section of the flexible shaft enabling selectable deflection of the distal end of the flexible shaft.

33. The system according to claim 32, wherein the steering mechanism comprises a steering tendon connected to the distal section of the flexible shaft, the steering tendon longitudinally disposed along the flexible shaft and accessible from a proximal end of the shaft.

34. The system according to claim 25, wherein the flexible shaft has an outer diameter ranging from about 8 French to about 10 French.

35. The system according to claim 25, wherein the open lumen is adapted to receive an implantable cardiac lead.

36. The system according to claim 25, wherein the open lumen is adapted to receive an injection of fluid.

* * * * *